United States Patent [19]
Chen

[11] Patent Number: 5,865,840
[45] Date of Patent: Feb. 2, 1999

[54] ENHANCEMENT OF LIGHT ACTIVATION EFFECT BY IMMUNE AUGMENTATION

[75] Inventor: James C. Chen, Bellevue, Wash.

[73] Assignee: Light Sciences Limited Partnership, Issaquah, Wash.

[21] Appl. No.: 955,939

[22] Filed: Oct. 22, 1997

[51] Int. Cl.[6] .................................................. A61N 5/06
[52] U.S. Cl. ............................................. 607/92; 604/49
[58] Field of Search ................................. 604/20–22, 49, 604/51; 607/92

[56] References Cited

U.S. PATENT DOCUMENTS 5,257,970  11/1993  Doudgerty ................................ 604/20
5,554,150   9/1996  Bousseau et al. ................... 604/891.1
5,649,904   7/1997  Gianni ......................................... 604/4

OTHER PUBLICATIONS de Vree, Wil J.A., et al., *Evidence for an Important Role of Neutrophils in the Efficacy of Photodynamic Therapy in Vivo,* Cancer Research, 56, 2908–2911, Jul. 1, 1996.

Mito, Keiichiro, *A needle type therapeutic system incorporating laser light and lumin for immunotherapy of cancer growing in deep organs,* Journal of Medical Engineering & Technology, vol. 20, No. 3 (May/Jun. 1996), pp. 121–126.

Krosl, Gorazd, et al., *Potentiation of Photodynamic Therapy–elicited Antitumor Response by Localized Treatment with Granulocyte–Macrophage Colony–stimulation Factor,* Cancer Research, 56, 3281–3286, Jul. 15, 1996.

Korbelik, Mladen, et al., *Enhanced Macrophage Cytotoxicity Against Tumor Cells Treated With Photodynamic Therapy,* Photochemistry and Photobiology, vol. 60, No. 5, pp. 497–502, 1994.

Ohara, Kiyoshi, M.D., et al., *Impact of Biological Clearance on Tumor Radioresponsiveness,* Int. J. Radiation Oncology Biol. Phys., vol. 34, No. 2, pp. 389–393, 1996, ©1996 Elsevier Science Inc.

Yamamoto, Nobuto, et al., *Photodynamic Immunopotentiation: in vitro Acitvation of Macrophages by Treatment of Mouse Peritoneal Cells with Haematoporphyrin Derivative and light,* Eur J Cancer, vol. 27, No. 4, pp. 467–471, 1991. Great Britain, ©1991 Pergamon Press plc.

Primary Examiner—John P. Lacyk
Assistant Examiner—Roy D. Gibson
Attorney, Agent, or Firm—Ronald M. Anderson

[57] ABSTRACT

The efficacy of a plurality of PDT treatments following at least an initial PDT treatment is enhanced by increasing the neutrophil count of the patient substantially above a normal level. The increase in the neutrophil count leads to a more rapid removal of dead abnormal cells and stroma that have been destroyed, thereby enabling light administered in subsequent PDT treatments to more effectively reach and destroy still living abnormal cells on the surface of the tumor. The accelerated removal of dead tumor cells also enables a more accurate assessment of the treatment progress, since the actual tumor size should be more evident in image of the site. By enabling a tumor to be more rapidly destroyed by multiple PDT treatments, the risk of metastatic spread of abnormal cells away from the treatment site is also reduced.

20 Claims, 1 Drawing Sheet

ENHANCEMENT OF LIGHT ACTIVATION EFFECT BY IMMUNE AUGMENTATION

FIELD OF THE INVENTION

This invention generally pertains to a method for enhancing an interaction between a patient's immunological system and a photodynamic therapy (PDT) that is delivered to a medical patient, and more specifically, to a method for enhancing the effects of PDT in destroying abnormal tissue in the body of a patient by administering a substance that increases the patient's white blood cell count.

BACKGROUND OF THE INVENTION

Abnormal cells in the body are known to selectively absorb certain dyes that have been perfused into a treatment site to a much greater extent than absorbed by surrounding tissue. For example, tumors of the pancreas and colon may absorb two to three times the volume of certain dyes, compared to normal cells. Once pre-sensitized by dye tagging in this manner, the cancerous or abnormal cells can be destroyed by irradiation with light of an appropriate wavelength or waveband corresponding to an absorbing wavelength or waveband of the dye, with minimal damage to surrounding normal tissue. The procedure that uses light to destroy undesirable tissue, known by the acronym PDT, has been clinically used to treat metastatic breast cancer, bladder cancer, lung carcinomas, esophageal cancer, basal cell carcinoma, malignant melanoma, ocular tumors, head and neck cancers, and other types of malignant tissue growths. Because PDT selectively destroys abnormal cells that have absorbed more of a photoreactive dye than normal cells, it can successfully be used to kill malignant tissue with less effect on surrounding benign tissue than alternative treatment procedures.

In typical applications of PDT, the light used in PDT is administered to an internal treatment site through an optical fiber from an external source such as a laser or is applied to a site exposed during a surgical procedure. However, alternative techniques exist to provide light therapy. For example, several different embodiments of implantable light emitting probes for administering photodynamic therapy (PDT) to an internal site within a patient's body are disclosed in commonly assigned U.S. Pat. No. 5,445,608. Further, a number of embodiments of flexible light emitting probes are disclosed in commonly assigned pending U.S. patent application, Ser. No. 08/613,390, and a continuation-in-part patent application thereof, Ser. No. 08/633,171, both entitled, "Flexible Microcircuits for Internal Light Therapy." The above-referenced U.S. Pat. No. 5,445,608 teaches that an implantable probe containing a plurality of light sources can be transcutaneously introduced to a desired treatment site through a surgical incision and then left in place for an extended period of time so that the light emitted by light emitting diodes (LEDs) or other types of light sources mounted in the probe can administer PDT to destroy abnormal tissue or other types of pathogenic organisms that have absorbed an appropriate photoreactive agent. Similarly, the flexible microcircuits disclosed in the above-noted pending patent applications are generally intended to be introduced into the body through a natural opening or through a small incision and positioned at the treatment site using conventional endoscopic techniques. The flexibility of these microcircuits facilitates their insertion into the body and disposition at the treatment site.

Several studies have investigated the relationship between the immunological system and PDT in the treatment of cancerous tumors. For example, in an article entitled "Evidence for an Important Role of Neutrophils in the Efficacy of Photodynamic Therapy in Vivo," Wil J. A. de Vree et al., Cancer Research, Vol. 56, pp. 2908–2911, Jul. 1, 1996, it is noted that administration of a granulocyte-colony stimulating factor (G-CSF) two days before PDT was started led to a fourfold increase in the number of circulating neutrophils and a retarded tumor growth in rats, compared to those injected with saline solution before receiving the PDT. The article postulates the following explanation for this effect.

" . . . (N)eutrophils might adhere via $\beta_2$-integrins to stretches in the vascular wall where endothelium as a result of PDT has contracted, and where the subendothelial matrix is exposed, as reported previously. Neutrophils, most likely attracted by chemotactic factors, could infiltrate the tumor area, releasing proteolytic enzymes that degrade attenuated tumor cells, which otherwise may continue to proliferate."

It is noted in the article that PDT had no effect on tumor growth in the absence of neutrophils—a condition achieved in the research by administering antigranulocyte antiserum.

In another article entitled "Potentiation of Photodynamic Therapy-elicited Antitumor Response by Localized Treatment with Granulocyte-Macrophage Colony-stimulating Factor," Gorazd Krosl et al., Cancer Research, Vol. 56, pp. 3281–3286, Jul. 15, 1996, the authors reported on experiments in which granulocyte-macrophage colony stimulating factor (GM-CSF) was administered three times in 48-hour intervals, beginning two days before PDT was administered and noted that the GM-CSF substantially improved the beneficial results of PDT in treating squamous cell carcinoma (SCCVII) cells. It was found that GM-CSF alone failed to provide any obvious benefit in treating a tumor. The research indicates that the GM-CSF treatment "increases the cytotoxic activity of tumor-associated macrophages against (SCCVII) tumor cells" and that "tumor-localized immune stimulation by GM-CSF amplifies a PDT-induced antitumor immune reaction, which has a potentiating effect on tumor control." It was noted that tumors treated with PDT are believed to be eradicated due to a combination of several different effects, including: (1) photooxidative damage to vital cellular structure; (2) inactivation of tumor cells by ischemia secondary to the damage of the tumor vasculature and by integrated tumoricidal activity of nonspecific and specific immune effector cells; and, (3) a host response dominated by a strong tumor-localized acute inflammatory reaction associated with the functional activation of tumor resident and newly arrived leukocytes. It is suggested by the reference that neutrophils, mast cells, monocytes, and macrophages participate in the antitumor activity in an early phase after PDT treatment, and that the release and phagocytosis of tumor cell debris following the destruction of tumor cells creates a condition for the processing and presentation of tumor antigens by macrophages and dendritic cells or other antigen-presenting cells, resulting in development of tumor-specific immunity.

In another article, "Enhanced Macrophage Cytotoxicity against Tumor Cells Treated with Photodynamic Therapy," Photochemistry and Photobiology, Vol. 60, No. 5, pp. 497–502, 1994, Mladen Korbelik and Gorazd Krosl, the authors report that they were led to investigate the cytotoxic activity of macrophages against PDT-treated target tumor cells based on related work performed by other researchers. Specifically, the article refers to earlier research indicating that due to the extensive damage of the membrane structure of tumor cells caused by PDT, affected tumor cells release alkylglycerols, lysophospholipids, and alkyllysophospholipids, which have been identified as potent macrophage stimulating agents. Release of these agents are thus believed to lead to an enhanced macrophagic destruction of tumor cells. The article reported that an enhanced macrophage-mediated killing of tumor cells treated by PDT was observed for two different types of macrophages, including peritoneal macrophages and macrophages differentiated from cells arrested at a promyelocytic stage by a leukemic transformation. However, experiments reported in this article indicate that the presence of PDT-treated tumor cells does not enhance the tumoricidal activity of macrophages directed against cells that are not treated with PDT.

None of the prior art reporting on the relationship of the immunologic system to PDT has explored the relationship between an enhanced neutrophil (white blood cell) count and a repetitive series of PDT treatments. Repetitive PDT treatments are most readily achieved with an implanted probe that can provide light therapy to adjacent abnormal tumor cells over an extended period of time. Even without modifying the body's immunologic response, such extended duration or repetitive PDT protocol has been found to provide substantial benefits relative to the more conventional approach of providing a single PDT treatment. As indicated above, prior research has shown that the efficacy of a single PDT treatment is enhanced by administering GM-CSF or G-CSF to a patient before the PDT treatment is provided. Various reasons have been advanced to explain these results. Although such explanations may prove correct, the prior research discussed above has not considered how administering GM-CSF or G-CSF after an initial PDT treatment might benefit subsequent PDT treatments and has not made any suggestions as to why such an approach might be of benefit.

SUMMARY OF THE INVENTION

In accord with the present invention, a method is defined for more effectively destroying abnormal tissue at a treatment site within a patient's body to improve the efficacy of PDT. The method includes the step of administering a plurality of light therapy treatments to the treatment site, at spaced-apart times. Each of the plurality of light therapy treatments destroys a portion of the abnormal tissue at the treatment site. A myeloid colony stimulating factor is administered to the patient after at least a first light therapy treatment has been administered. The myeloid colony stimulating factor enhances removal of the portion of abnormal tissue that has been destroyed by any prior light therapy treatment, exposing abnormal tissue at the treatment site that has not yet been destroyed. In this manner, the effectiveness of a subsequent light therapy treatment in destroying the remaining abnormal tissue is enhanced.

The method preferably further includes the step of administering an additional amount of the myeloid colony stimulating factor to the patient following subsequent light therapy treatments. The additional myeloid colony stimulating factor enhances the removal of the portion of abnormal tissue that has been destroyed by any prior light therapy treatments. The myeloid colony stimulating factor accelerates the biological removal of necrotic tissue and apoptotic tissue comprising the abnormal tissue destroyed by the prior light therapy treatment, by elevating a white blood cell count in the patient's body, which enhances a phagocytic response by white blood cells at the treatment site. Further, the myeloid colony stimulating factor administered preferably comprises either G-CSF or GM-CSF.

The step of administering the plurality of light therapy treatments includes the step of administering a photoreactive agent to the treatment site. The photoreactive agent is selected for one or more characteristic wavebands of light absorption. Light having one or more emission wavebands substantially corresponding to the characteristic waveband of light absorption of the photoreactive agent is applied to the treatment site during each of the plurality of light therapy treatments. The light is absorbed by the photoreactive agent, which then destroys the abnormal tissue. Light can be administered from a light source implanted within the abnormal tissue, or disposed adjacent to the abnormal tissue. The enhanced removal of this tissue that has been destroyed reduces the overall mass of the abnormal tissue. A corresponding reduction in the distance between the light from the implanted light source and a periphery of the abnormal tissue enables the light from the source to more effectively be transmitted to the periphery of the abnormal tissue.

The myeloid colony stimulating factor also reduces the time between successive light therapy treatments. Consequently, a repopulation of the treatment site by the abnormal tissue between the successive light therapy treatments that would otherwise occur due to regrowth of the abnormal tissue is reduced.

The method may also include the step of imaging the treatment site to evaluate an effectiveness of the plurality of light therapy treatments in destroying the abnormal tissue. The enhanced removal of the abnormal tissue that has been destroyed increases the clarity with which the treatment site is imaged, since only the remaining abnormal tissue appears. Imaging may be accomplished using an ultrasound modality, a computer tomography modality, or a magnetic resonance imaging modality. The enhanced removal of the abnormal tissue that has been destroyed also should reduce a risk of a metastatic spread of the abnormal tissue away from the treatment site to a disparate part of the patient's body.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1 is schematic illustration of a tumor, showing an implanted light source delivering a PDT treatment internally to the tumor, where either GM-CSF or G-CSF has been administered at least after one such PDT treatment has occurred; and FIG. 2 is a schematic illustration of a tumor, showing a light source delivering a PDT treatment to an outer surface of the tumor, where either GM-CSF or G-CSF has been administered at least after one such PDT treatment has occurred.

DESCRIPTION OF THE PREFERRED EMBODIMENT

Figure 1:
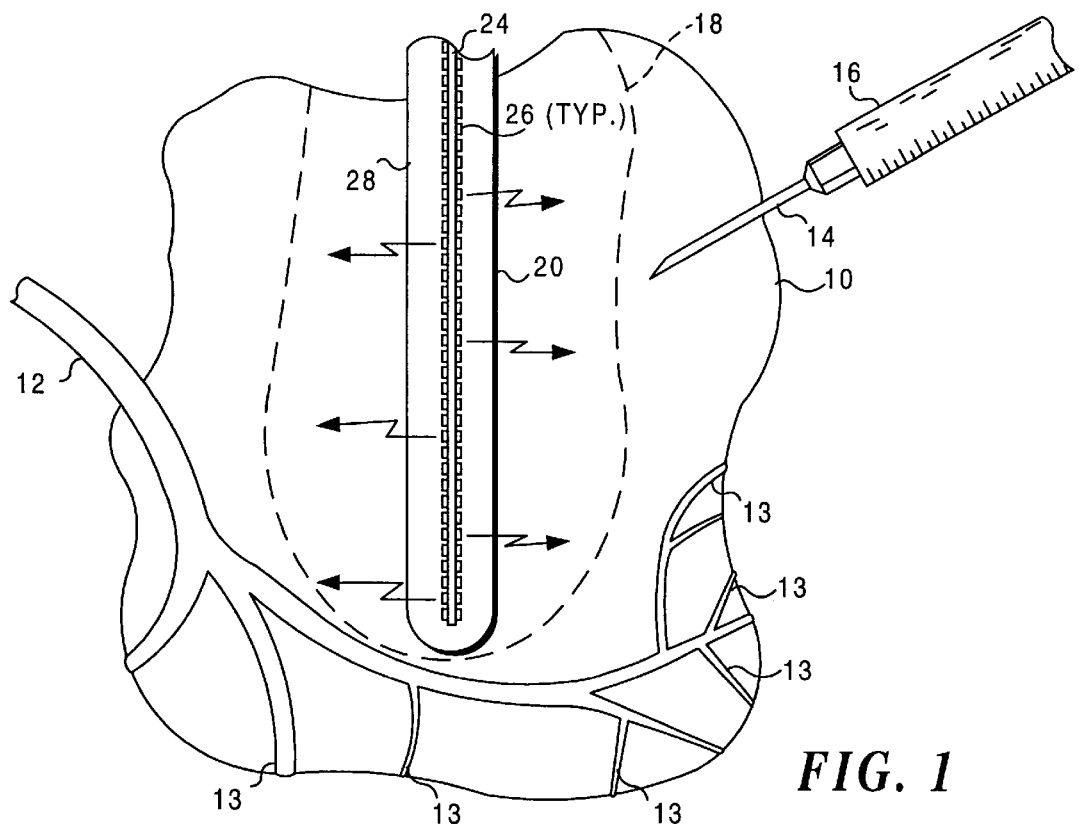

As noted above in the Background of the Invention, it is believed that damage to tumor cells resulting from administration of PDT tends to attract macrophages that destroy the damaged tumor cells. Another aspect of the immunologic system that is not discussed in the prior art relative to PDT relates to the response of the immunologic system to necrosis and apoptosis, for tissue destroyed by PDT. Necrosis refers to the process in which cells release an inflammatory agent after they have been destroyed. Apoptosis refers to cells that do not release an inflammatory agent after being destroyed. The white cells or neutrophils in the body thus provide a scavenging function by clearing away both necrotic or apoptotic cells.

When PDT destroys cells, the white blood cells respond to necrosis and apoptosis of the dead tumor cells just as they do for any other dead cells. The time required for the clearance of cells that have been destroyed by PDT whenever a single PDT treatment is applied is not particularly important. However, in the present invention, it is contemplated that a plurality of PDT treatments will be delivered over an extended period of time, and the intent of the present invention is to enable the repeated PDT treatment to more effectively destroy a tumor or other abnormal tissue within a patient's body. To achieve this goal, the present invention enhances the neutrophil count and thereby increases the rate at which neutrophils carry out the scavenging process and remove destroyed tumor cells.

In a process in which a plurality of successive PDT treatments are delivered to a treatment site within a patient's body, the effectiveness of each successive treatment will clearly be improved by insuring that the light applied during the treatment reaches the abnormal cells that are yet to be destroyed and is not blocked by tumor cells that have already been destroyed during a previous PDT treatment. If tumor cells that were destroyed during a previous PDT treatment have not yet been removed from the treatment site by the action of neutrophils, the subsequent PDT treatment is less effective. By enhancing the rate at which tumor cells destroyed by a previous PDT treatment are removed from the site, it will be apparent that the next PDT treatment will be more effective, since the light administered during the next treatment will be applied directly to the tumor cells that are still alive.

Several other advantages are believed likely to result from increasing the neutrophil count after an initial PDT treatment has destroyed some of the tumor cells at a treatment site. One potential advantage is that the removal of necrotic and apoptotic tissue by the increased number of neutrophils will likely reduce interstitial tumor pressure, thereby improving the delivery of drugs to the tumor site, particularly, the photoreactive agent employed for a successive PDT treatment. In addition, the reduced interstitial tumor pressure will enhance the delivery of oxygen to the tumor, by increasing blood flow to the tumor. It is generally believed that singlet oxygen produced during a PDT treatment is involved in the destruction of abnormal cells. The increase in oxygen delivery to a tumor will thus likely increase this desired action.

In addition, a reduction of tumor mass effected by an enhanced count of white blood cells in a patient's body should reduce the tumor mass, thereby enabling light to be transmitted to the tumor periphery more readily than would be possible without the removal of the destroyed tumor cells by the neutrophils. By thus reducing the tumor mass, the distance between the boundary of the tumor and the light source administering light during the next PDT treatment should be substantially reduced. Also the efficacy of each subsequent PDT treatment in a cycle of a plurality of such treatments is enhanced because the present invention improves light and photoreactive agent dosimetry, specifically by improving the penetration and distribution of the light and drug at the treatment site, thereby substantially reducing the risk of metastatic spread of abnormal cells from the treatment site to other portions of the body.

Since the increased neutrophil count tends to shorten the time between PDT treatments, a more rapid tumor clearance can be achieved that reduces and prevents repopulation of the tumor at the treatment site. Repopulation of tumor cells at a treatment site tend to be a prime cause of failure of local tumor control, particularly when a single PDT treatment is applied to a tumor.

Certain types of drugs that may be administered to a patient can cause an abnormally low neutrophil count. In such cases, the PDT treatment and successive treatments may not cause the overall size of the tumor to decrease or change significantly. In contrast, by enhancing the neutrophil count well above that typically found in a "normal" patient's body, the advantages noted above can be achieved, thereby greatly increasing the benefits of repetitive PDT treatments. For example, in a patient who has received chemotherapy or radiation therapy, the drugs administered substantially reduce the neutrophil count due to bone marrow suppression. By enhancing the neutrophil count while treating a tumor in such patients using the present invention, a substantial reduction of implant infection risk can be achieved, in addition to enhancing the efficacy with which the tumor is destroyed.

Figure 2:
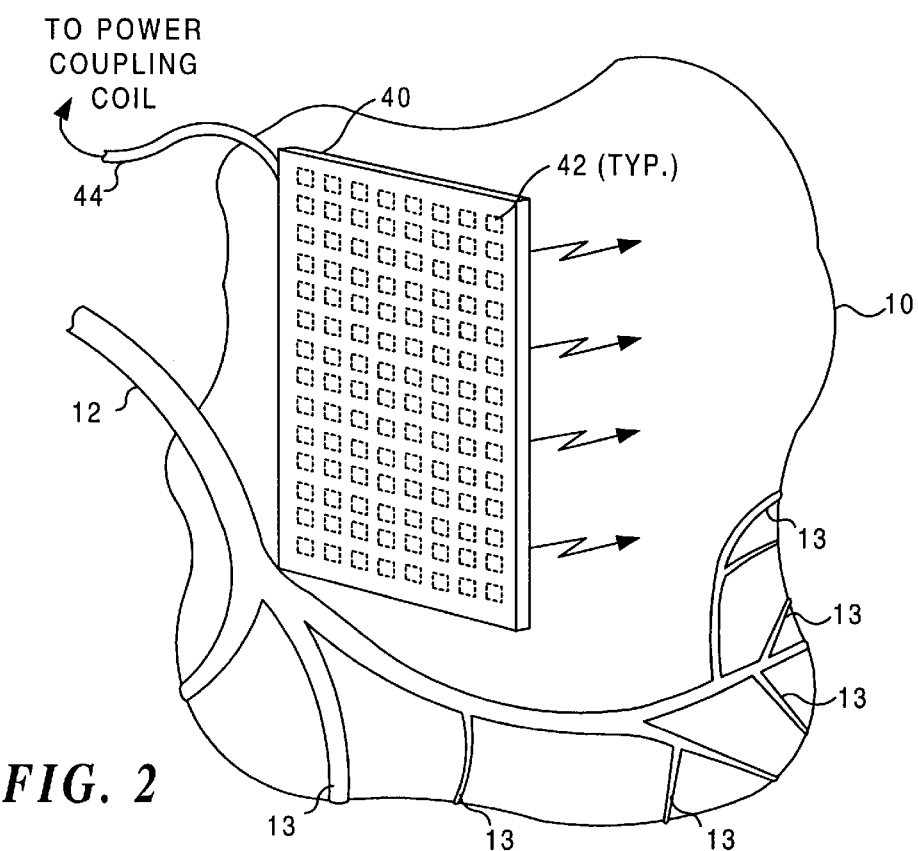

FIGS. 1 and 2 illustrate how the present invention is employed to achieve improved efficacy during the course of a plurality of PDT treatments delivered to a tumor 10. In FIG. 1, tumor 10 is supplied blood through one or more main vessels 12, having a plurality of branching vessels 13. Only one such vessel is illustrated to simplify the figure. Because the cells comprising tumor 10 are abnormal, it tends to grow at a relatively rapid rate and if left unchecked, the condition may lead to a metastatic spread of the abnormal cells throughout a patient's body.

To administer PDT treatments to tumor 10 in the example shown in FIG. 1, an elongate probe 20 is implanted internally within tumor 10 during a conventional surgical or endoscopic procedure. Probe 20 may be either rigid or flexible, as appropriate to the technique used to facilitate its placement within tumor 10 and depending upon the location of the tumor within the patient's body. Probe 20 includes a plurality of light sources 26, e.g., LEDs, which are disposed on opposite sides of a substrate 24. Details such as the electrically conductive traces that convey electrical current to each of the light sources are not shown. An optically transparent and biocompatible sheath 28 encloses light sources 26 and substrate 24, but allows light emitted by the light sources to be transmitted through to an interior surface 18 of the tumor.

In FIG. 1, a syringe 16 is illustrated; the syringe includes a needle 14 that is inserted into tumor 10 to infuse a photoreactive agent, such as porphyrin, into the treatment site. Alternatively, the porphyrin or other photoreactive agent can be administered intravascularly. The photoreactive agent is selectively absorbed by the abnormal cells comprising tumor 10 to a much greater extent than by surrounding normal cells. Light emitted by light sources 26 has a characteristic waveband that is substantially equal to an absorption waveband of the photoreactive agent. Thus, tumor cells that have absorbed the photoreactive agent are destroyed by the light emitted from probe 20.

After one or more PDT treatments has been administered, syringe 16 is used to administer either G-CSF or GM-CSF to the patient (but not into the tumor as shown in FIG. 1) in multiple injections delivered over a period of time, to stimulate the production of white blood cells by the patient's bone marrow. The G-CSF or GM-CSF thus causes the neutrophil count within the patient's immunologic system to be substantially elevated. The additional white blood cells delivered through vessel 12 suffuse the abnormal cells comprising tumor 10 and more rapidly and completely carry away necrotic and apoptotic material comprising dead abnormal cells and stroma resulting from the previous PDT treatment. Successive PDT treatments that are delivered are more effective in destroying the tumor as a result of the light being able to reach abnormal cells comprising the tumor on internal surface 18 surrounding implanted probe 20. The advantages of the enhanced neutrophil or white blood cell count noted above are thus achieved for the successive PDT treatments.

FIG. 2 illustrates the use of a generally planar substrate probe 40 that includes a plurality of light sources 42, again preferably comprising LEDs. Light sources 42 are mounted on substrate 40 in a spaced-apart array that covers the surface of the substrate so that light emitted by the light sources is generally directed toward the outer surface of tumor 10. A biocompatible, optically transparent sheath (not shown) encloses the light sources and the conductive traces (also not shown) that convey electrical current to the light sources to energize them.

Syringe 16 (FIG. 1) is used for administering the photoreactive agent that selectively is absorbed by the abnormal cells comprising tumor 10 before the light is administered to the tumor from light sources 42. The light emitted by light sources 42 has a characteristic wavelength or waveband corresponding to the absorption wavelength or waveband of the photoreactive agent preferentially absorbed by the abnormal cells and thus kills the abnormal cells without having significant effect on any normal cells of the surrounding tissue. Once at least an initial PDT treatment has then been delivered, killing some of the abnormal tumor cells, the G-CSF or GM-CSF is administered to the patient with the syringe in a plurality of injections over a period of time. These injections enhance the neutrophil count to achieve the beneficial results discussed above.

Although not shown in either Figure, it is also contemplated that an optical fiber can be used to administer light to a treatment site (e.g., tumor 10) within the patient's body from an external light source such as a laser. Other types of light sources can be used either in connection with implanted probes like those shown in FIGS. 1 and 2, or to provide light from outside the patient's body. The only significant requirement is that the light source produce light having a characteristic waveband corresponding to that of the photoreactive agent administered to the patient to implement the PDT.

If an implanted probe is employed, electrical power can be supplied to energize the probe from outside the patient's body using an external power source that is connected to a coil applied on the outer surface of the patient's skin, generally opposite an internally implanted coil that is connected to the implanted probe (neither shown), for example, through a line 44 as illustrated in FIG. 2. A similar arrangement can be used to provide power and other signals to implanted probe 20, in FIG. 1. Other details related to the use of implanted probes and other designs for flexible implanted probes are disclosed in commonly assigned pending U.S. patent application, Ser. No. 08/613,390, and a continuation-in-part patent application thereof, Ser. No. 08/633,171, both entitled, "Flexible Microcircuits for Internal Light Therapy."

An exemplary schedule for implementing the steps of the present invention is as follows. On the first day of the procedure, a photoreactive agent is administered to the patient, either intravascularly, or to the treatment site (intratumorously). On the next day, an initial PDT treatment is administered, using either an implanted probe like that shown in either FIGS. 1 or 2, or an external light source that supplies light to the treatment site from outside the patient's body. After at least the initial PDT treatment, for example, starting on the third day of the procedure, the G-CSF or GM-CSF factor is given on a daily basis, through about the tenth day of the procedure. It is contemplated that the amount and frequency with which the G-CSF or GM-CSF is administered and the amount of the dosage can be determined by monitoring the neutrophil count in the patient. After the administration of the G-CSF or GM-CSF has begun, for example, on the fourth day following the start of the procedure, a series of additional PDT treatments are initiated. The tumor response to the plurality of PDT treatments can be assessed at any time during the procedure by imaging the tumor using ultrasound, CT, MRI, or other imaging modality. One of the advantages of the present invention is that it enables a more accurate assessment of the treatment progress in destroying the tumor by enabling the true tumor size to be accurately evaluated using such imaging modalities. Based on the assessment of the effectiveness of the plurality of PDT treatments that have been administered, a decision can be made as to whether the procedure should be repeated. It is contemplated that to insure the total destruction of the tumor, the procedure should be repeated at least one time.

It should be emphasized that the G-CSF or GM-CSF is not administered until after the start of the PDT therapy has begun. This ensures that the resulting increased neutrophil count is applied in clearing dead abnormal tumor cells from the treatment site, to improve the beneficial effects of subsequent PDT treatments. The dosage range for G-CSF and GM-CSF are variable, as generally well known to oncologists. It is contemplated that if the neutrophil count rises to a level equal to or greater than about 50,000/microliter, the next dose of G-CSF or GM-CSF may be held off until the white count has fallen below this level and then resumed on a daily basis, pending the monitored neutrophil count. It should also be understood that the preceding example will likely be modified depending upon the clinical tumor response, patient condition, and neutrophil count. By thus increasing the neutrophil count in carrying out the procedure of the present invention, it is more likely that complete destruction of the tumor can be achieved and the risk of metastatic spread of the abnormal cells throughout the patient's body will be minimized.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for more effectively destroying abnormal tissue at a treatment site within a patient's body, comprising the steps of:
   (a) administering a plurality of light therapy treatments to the treatment site, at spaced-apart times, each of the plurality of light therapy treatments destroying a portion of the abnormal tissue at the treatment site; and
   (b) administering a myeloid colony stimulating factor to the patient after a first light therapy treatment of the plurality of light therapy treatments has been administered to the treatment site, said myeloid colony stimulating factor enhancing removal of the portion of abnormal tissue that has been destroyed by any prior light therapy treatment, and thereby exposing abnormal tissue at the treatment site that has not yet been destroyed so that an effectiveness of a subsequent light therapy treatment in destroying the abnormal tissue is enhanced.

2. The method of claim 1, further comprising the step of administering an additional amount of the myeloid colony stimulating factor to the patient following others of the plurality of light therapy treatments, to further enhance the removal of the portion of abnormal tissue that has been destroyed by any prior light therapy treatments.

3. The method of claim 1, wherein the myeloid colony stimulating factor accelerates biological removal of necrotic tissue and apoptotic tissue from the portion of the abnormal tissue destroyed by the prior light therapy treatment, by elevating a white blood cell count in the patient's body and enhances a phagocytic response by white blood cells at the treatment site.

4. The method of claim 1, wherein the step of administering the plurality of light therapy treatments comprises the steps of:
 (a) administering a photoreactive agent to the treatment site, said photoreactive agent being selected for one or more characteristic wavebands of light absorption; and
 (b) applying light to the treatment site during each of the plurality of light therapy treatments, said light having one or more emission wavebands substantially corresponding to the characteristic waveband of light absorption of the photoreactive agent and being absorbed by the photoreactive agent, which then destroys the abnormal tissue at the treatment site.

5. The method of claim 1, wherein the myeloid colony stimulating factor reduces the time between successive light therapy treatments and thereby reduces repopulation of the treatment site by the abnormal tissue between the successive light therapy treatments that would otherwise occur due to regrowth of the abnormal tissue.

6. The method of claim 1, further comprising the step of imaging the treatment site to evaluate an effectiveness of the plurality of light therapy treatments in destroying the abnormal tissue, the enhanced removal of the abnormal tissue that has been destroyed increasing an efficacy with which the treatment site is imaged.

7. The method of claim 6, wherein the step of imaging comprises the step of effecting one of an ultrasound modality, a computer tomography modality, and a magnetic resonance imaging modality.

8. The method of claim 1, wherein the enhanced removal of the abnormal tissue that has been destroyed reduces a risk of a metastatic spread of the abnormal tissue away from the treatment site to a disparate part of the patient's body.

9. The method of claim 1, wherein the myeloid colony stimulating factor administered comprises one of a granulocyte colony stimulating factor and granulocyte macrophage colony stimulating factor.

10. The method of claim 1, wherein the step of administering the plurality of light therapy treatments comprises the step of implanting a light source within the abnormal tissue.

11. The method of claim 10, wherein the enhanced removal of the abnormal tissue that has been destroyed reduces a mass of the abnormal tissue, enabling light to more effectively be transmitted to a periphery of the abnormal tissue by reducing a distance between the light source that is implanted and the periphery of the abnormal tissue.

12. A method for enhancing a repetitive light therapy modality used to destroy abnormal tissue in a tumor disposed in a body of a patient, comprising the steps of:
 (a) administering a photoreactive agent to the tumor, said photoreactive agent being selected for one or more characteristic wavebands of light absorption;
 (b) repetitively applying light to the tumor in a series of treatments, said light having one or more emission wavebands substantially corresponding to the characteristic waveband of light absorption of the photoreactive agent and being absorbed by the photoreactive agent to destroy the abnormal tissue at the treatment site; and
 (c) after at least a first treatment in the series of treatments in which light is applied to the tumor, administering a myeloid colony stimulating factor, said myeloid colony stimulating factor promoting an increase in a neutrophil count within the body of the patient, said increase in the neutrophil count resulting in an enhanced removal of the abnormal tissue that has been destroyed by previously applying light to the tumor and thereby improving an efficacy of subsequent treatments in the series of treatments in which light is applied to the tumor.

13. The method of claim 12, wherein the myeloid colony stimulating factor is administered in sufficient dosage and sufficiently often to achieve a predetermined neutrophil count in the body of the patient.

14. The method of claim 12, wherein the step of repetitively applying light comprises the step of implanting a light source adjacent to the tumor to apply the light.

15. The method of claim 14, wherein the light source is implanted within the tumor.

16. The method of claim 12, wherein the increased neutrophil count increases a rate at which necrotic and apoptotic tissue destroyed by the repetitive application of the light to the tumor is removed by the neutrophils, thereby exposing abnormal tissue that has not yet been destroyed to a subsequent application of light to the tumor, so that the efficacy of the subsequent light treatments is improved.

17. The method of claim 12, wherein the myeloid colony stimulating factor comprises one of a granulocyte myeloid colony stimulating factor and a granulocyte macrophage myeloid colony stimulating factor.

18. The method of claim 12, further comprising the step of reducing a time between repetitive applications of the light to the tumor compared to that used if the myeloid colony stimulating factor has not been administered.

19. The method of claim 12, wherein the increase in the neutrophil count also reduces a risk of infection in the body of the patient.

20. The method of claim 12, wherein the increase in the neutrophil count also reduces a risk of a metastatic spread of the tumor to other parts of the body of the patient.

* * * * *